US00PP37431P2

(12) United States Plant Patent
Boxriker

(10) Patent No.: US PP37,431 P2
(45) Date of Patent: May 19, 2026

(54) ***DAHLIA* PLANT NAMED 'KLEDH24716'**

(50) Latin Name: ***Dahlia* sp.**
Varietal Denomination: KLEDH24716

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/320,318

(22) Filed: Sep. 5, 2025

(51) Int. Cl.
*A01H 5/02* (2018.01)

(52) U.S. Cl.
USPC ..... Plt./321

(58) Field of Classification Search
USPC ..... Plt./321
CPC ..... A01H 6/144; A01H 5/02
See application file for complete search history.

*Primary Examiner* — Keith O. Robinson
(74) *Attorney, Agent, or Firm* — Weatherly IP Solutions, LLC; Karen P. Bechtold; James M. Weatherly

(57) ABSTRACT

A new *Dahlia* plant named 'KLEDH24716' particularly distinguished by purple and magenta colored flowers with white tips, a daisy-eyed composite head inflorescence held above the foliage, and a semi-upright growing habit, as described herein.

1 Drawing Sheet

Genus and species: *Dahlia* sp.
Variety denomination: 'KLEDH24716'.

BACKGROUND

The present invention comprises a new and distinct variety of *Dahlia*, botanically known as *Dahlia* sp., and hereinafter referred to by the variety name 'KLEDH24716'. 'KLEDH24716' originated from an open pollination with the female *Dahlia* 'DATRETTEN' (U.S. Plant Pat. No. 18,971) and an unknown male *Dahlia* plant in Summer 2019 in Latina, Italy. In April 2020, in Latina, Italy, a seedling was selected and named 'KLEDH24716'. 'KLEDH24716' was first vegetatively propagated by vegetative cuttings in May 2020 in Latina, Italy. 'KLEDH24716' was found to reproduce true to type in successive generations of asexual propagation in Italy, Germany, Tenerife and Uganda.

SUMMARY

The following are the most outstanding and distinguishing characteristics of 'KLEDH24716' when grown under normal horticultural practices in Latina, Italy.

1. Purple and magenta-colored flowers with white tips
2. A daisy-eyed composite head inflorescence held above the foliage
3. A semi-upright growing habit

DESCRIPTION OF THE PHOTOGRAPH

This new *Dahlia* plant is illustrated by the accompanying photograph of the plant approximately fourteen weeks old and grown in a greenhouse in Stuttgart, Germany. The photograph shows the whole plant, including the inflorescences and foliage and buds and was taken in May 2024 in Stuttgart, Germany. The colors shown are as true as can be reasonably obtained by conventional photographic procedures.

DESCRIPTION OF 'KLEDH24716'

The following detailed descriptions set forth the distinctive characteristics of 'KLEDH24716'. The data which define these characteristics were collected from asexual reproductions from 16-week-old plants grown in a greenhouse in Latina, Italy. Color references are to The R.H.S. Colour Chart of The Royal Horticultural Society of London (R.H.S.), 5$^{th}$ edition (2007).

Classification:
- *Family*.—Asteraceae.
- *Botanical*.—*Dahlia* sp.
- *Designation*.—'KLEDH24716'.

Parentage:
- *Female parent*.—'DATRETTEN' (U.S. Plant Pat. No. 18,971).
- *Male parent*.—Unknown male parent.

Propagation:
- *Type*.—Vegetative terminal cuttings.
- *Time to produce a rooted young plant*.—3 to 4 weeks.
- *Time to produce a flowering plant*.—About 9 weeks.
- *Root description*.—RHS N155C in color, fine.
- *Rooting habit*.—Freely branching and moderately dense.

Plant description:
- *Plant and growth habit*.—Semi-upright.
- *Plant height*.—To the top of foliar plane: About 14.0 cm. Including inflorescence: About 22.0 cm.
- *Plant diameter*.—About 28.0 cm.

Lateral branches:
- *Length*.—Up to the last pair of leaves: About 10.0 cm. Including inflorescence: About 20.0 cm.
- *Diameter*.—0.3 cm.
- *Internode length*.—Up to 4.0 cm.
- *Strength*.—Medium strong.
- *Texture*.—Smooth.
- *Color*.—Close to RHS 144B.

Foliage description:
- *Arrangement*.—Opposite, mostly simple, pinnate at the base.
- *Length*.—About 13.0 cm.
- *Width*.—About 7.0 cm.
- *Shape*.—Ovate.
- *Apex*.—Acuminate.
- *Base*.—Obtuse.

*Margin*.—Serrate.
*Venation pattern*.—Arcuate.
*Venation color*.—Close to RHS 147B.
*Texture*.—Upper and lower surface: Slightly hairy on the edges, slightly rugose and glossy.
*Color*.—Immature: Upper surface: Close to RHS N137A. Lower surface: Close to RHS 191A. Mature: Upper surface: Close to RHS N137A and N137B. Lower surface: Close to RHS 194A.

Petioles:
*Length*.—Up to 2.5 cm.
*Diameter*.—About 0.4 cm.
*Texture*.—Upper surface: Smooth. Lower surface: Smooth.
*Color*.—Upper surface: Close to RHS 146C. Lower surface: Close to RHS 146D.

Inflorescence description:
*Appearance and arrangement*.—Composite head inflorescence, daisy-eyed, held above the foliage.
*Fragrance*.—Not detected.
*Time to flower*.—About 9 weeks after potting in greenhouse conditions.
*Post-production longevity*.—Plants flower continuously from spring through autumn.

Inflorescence bud:
*Height*.—About 1.3 cm.
*Diameter*.—About 1.4 cm.
*Shape*.—Globular, shortly oblong.
*Color*.—RHS 144A at the base and RHS 144C toward the tips.

Inflorescence size:
*Diameter*.—About 7.0 cm.
*Depth* (*height*).—About 2.0 cm.
*Disc diameter*.—About 0.6 cm.
*Receptacle height*.—About 0.4 cm.
*Receptacle diameter*.—About 1.5 cm.
*Receptacle color*.—Close to RHS 137C.

Ray florets:
*Quantity per inflorescence*.—Approximately 70 in about 7 whorls.
*Length*.—About 2.8 cm.
*Width*.—About 1.3 cm.
*Shape*.—Elliptic.
*Apex*.—Pointed.
*Base*.—Fused in a tube.
*Margin*.—Entire.
*Aspect*.—Keeled.
*Texture*.—Upper surface: Smooth. Lower surface: Smooth.
*Color*.—Immature: Upper surface: Close to RHS 72A, a bit darker and more shiny, sometimes close to RHS 73D at the tips. Lower surface: Close to RHS 72A and RHS 69D at the tips and along the keels. Mature: Upper surface: Close to RHS 72A, and close to RHS N78B at the distal quarter Lower surface: RHS 72A and RHS N80B at the distal quarter; RHS 76B along the keels.

Disc florets:
*Quantity per inflorescence*.—35.
*Length*.—About 1.3 cm.
*Diameter*.—About 0.15 cm.
*Shape*.—Tubular.
*Texture*.—Inner surface: Smooth. Outer surface: Smooth.
*Color*.—Immature: Inner surface: Close to RHS 13B. Outer surface: Close to RHS 13B. Mature: Inner surface: Close to RHS 13B. Outer surface: Close to RHS 13B.

Phyllaries:
*Quantity per inflorescence*.—5 to 7 at the external whorl, 12 in the internal whorl.
*Length*.—External: About 1.0 cm. Internal: About 1.6 cm.
*Width*.—External: About 0.45 cm. Internal: About 0.6 cm.
*Shape*.—Lanceolate to spatulate.
*Apex*.—Obtuse.
*Base*.—External: Attenuate. Internal: Fused.
*Margin*.—Entire.
*Texture*.—Upper surface: Smooth and slightly glossy. Lower surface: Smooth and slightly glossy.
*Color*.—Upper surface: External whorl: RHS N137A. Internal whorl: RHS 141A at the base to RHS 144C at the tips. Lower surface: External whorl: RHS N137B. Internal whorl: RHS 137A at the base to RHS 144C at the tips.

Peduncles:
*Length, terminal peduncle*.—Up to 8.5 cm.
*Length, axillary peduncle*.—Up to 7.0 cm.
*Diameter*.—About 0.25 cm.
*Strength*.—Medium strong.
*Texture*.—Smooth.
*Color*.—Close to RHS 146A.

Reproductive organs:
*Androecium*.—Quantity per floret: 5 stamens with fused anthers. Filament length: About 0.3 cm. Filament color: Close to RHS 145D. Anther shape: Oblong. Anther length: 0.4 cm. Anther color: RHS 21A. Pollen amount: Abundant. Pollen color: RHS 21A.
*Gynoecium*.—Quantity per floret: 1. Pistil length: About 1.5 cm. Style length: About 0.8 cm. Style color: RHS 145D. Stigma shape: Bipartite. Stigma color: RHS 21A. Ovary color: RHS 145C.

Fruit and seed set: Not observed during growing season.

Disease and pest/insect resistance: No disease resistance observed.

COMPARISON OF 'KLEDH24716' WITH PARENTAL LINE AND KNOWN VARIETY

'KLEDH24716' is distinguished from the parent as described in Table 1.

TABLE 1

Comparison with Parental Line

| Trait | Variety 'KLEDH24716' | Female parent 'DATRETTEN' (U.S. Plant Pat. No. 18,971) |
|---|---|---|
| Flower color | Purple and magenta with white tips | Red with white tips |

'KLEDH24716' can be compared to the commercial *Dahlia* variety. 'KLEDH24725' (unpatented). Differences between the varieties are described in Table 2.

TABLE 2

Comparison with Similar Variety

| Trait | Variety 'KLEDH24716' | Commercial line 'KLEDH24725' (unpatented) |
|---|---|---|
| Flower color | Purple and magenta with white tips | Light pink and white with varying color proportions |

I claim:

1. A new and distinct variety of *Dahlia* plant named 'KLEDH24716' as shown and described herein.

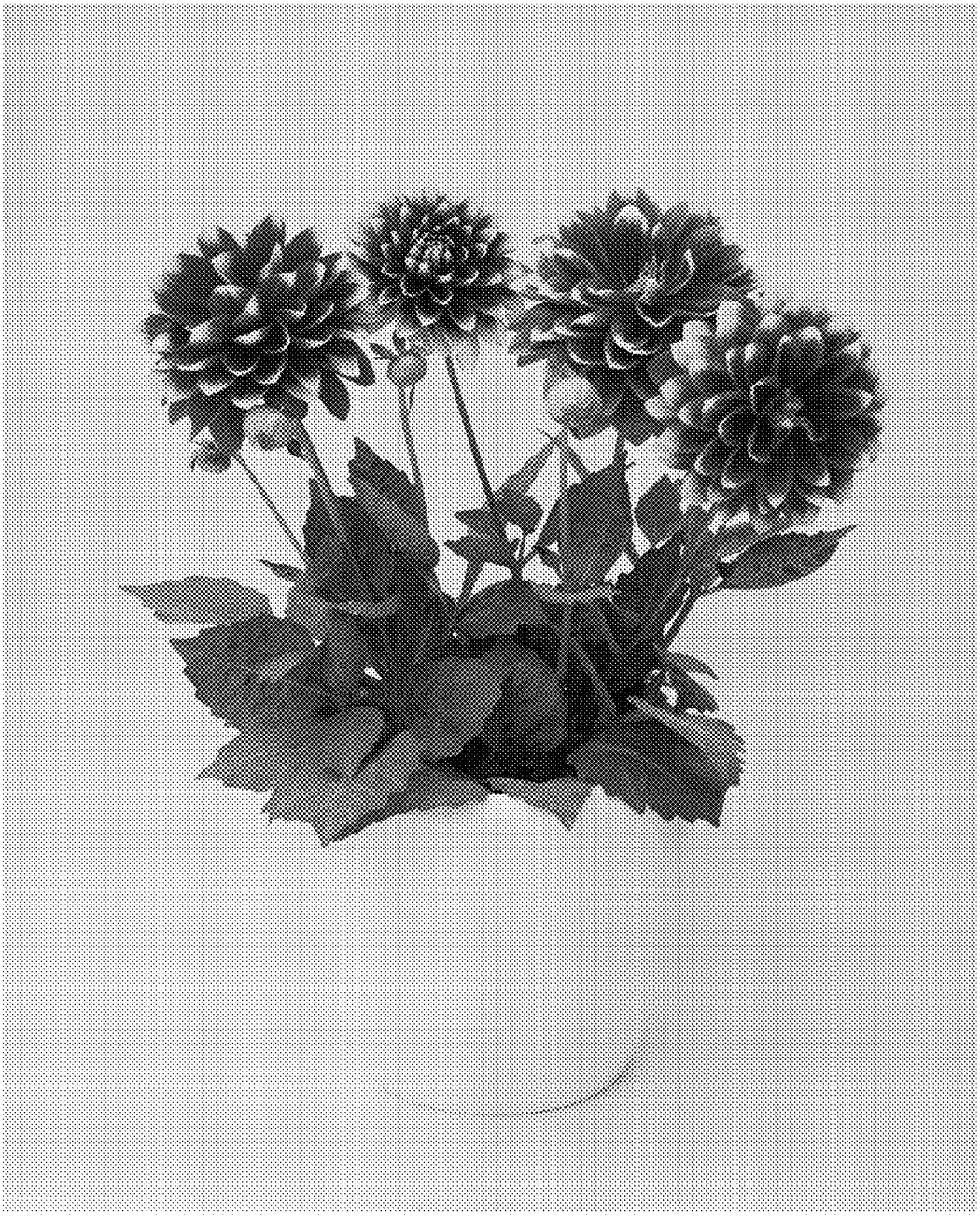

* * * * *